United States Patent [19]

Umeda

[11] Patent Number: 4,723,864
[45] Date of Patent: Feb. 9, 1988

[54] ENDOSCOPE AND PHOTOGRAPHING APPARATUS

[75] Inventor: Hiroyuki Umeda, Kasukabe, Japan

[73] Assignee: Kabushiki Kaisha Machida Seisakusho

[21] Appl. No.: 789,184

[22] Filed: Oct. 18, 1985

[30] Foreign Application Priority Data

Dec. 14, 1984 [JP] Japan .................. 59-263038

[51] Int. Cl.⁴ .................................. F16D 1/00
[52] U.S. Cl. .................... 403/322; 403/344; 128/4; 354/62
[58] Field of Search .......... 403/344, 338, 322; 128/4, 6, 8; 354/62

[56] References Cited

U.S. PATENT DOCUMENTS 4,066,330 1/1978 Jones ..................... 403/322 X
4,305,386 12/1981 Tawara ................... 128/4
4,413,278 11/1983 Feinbloom ............. 354/62 X Primary Examiner—Andrew V. Kundrat
Attorney, Agent, or Firm—Kane, Dalsimer, Kane, Sullivan and Kurucz

[57] ABSTRACT

A connector device is disclosed for detachably connecting a photographing apparatus to an endoscope eyepiece barrel. A pair of clamping links have their respective one ends pivotally mounted on an attaching ring adapted to be secured to the photographing apparatus, and are movable between an open position where the links are out of a space in the attaching ring for receiving an eyepiece barrel end flange and a closed position where the links extend into the space. The links are biased toward each other by a resilient element. A pair of support links have their respective one ends pivotally connected to each other and the respective other ends pivotally connected to the respective other ends of the clamping links, respectively. A stopper mechanism maintains the connecting point between the support links in a position between an axis of the attaching ring and a line passing through the two connecting points between the clamping and support links, and maintains, against the resilient element, the clamping links in the open posiiton. As the end flange is inserted into the space, the moving force of the end flange is converted by a force converting mechanism into a force for releasing the clamping and support links from the stopper mechanism to urge the connecting point between the support links to a position beyond the line, to thereby allow the clamping link to be moved by the resilient element from the open position to the closed position.

13 Claims, 14 Drawing Figures

ENDOSCOPE AND PHOTOGRAPHING APPARATUS

BACKGROUND OF THE INVENTION

Field of the Invention

The present invention relates to a connector device adapted to be secured to a photographing apparatus for detachably connecting the same to an end flange on an eyepiece barrel of an endoscope.

RELATED ART STATEMENT

Figure 13:
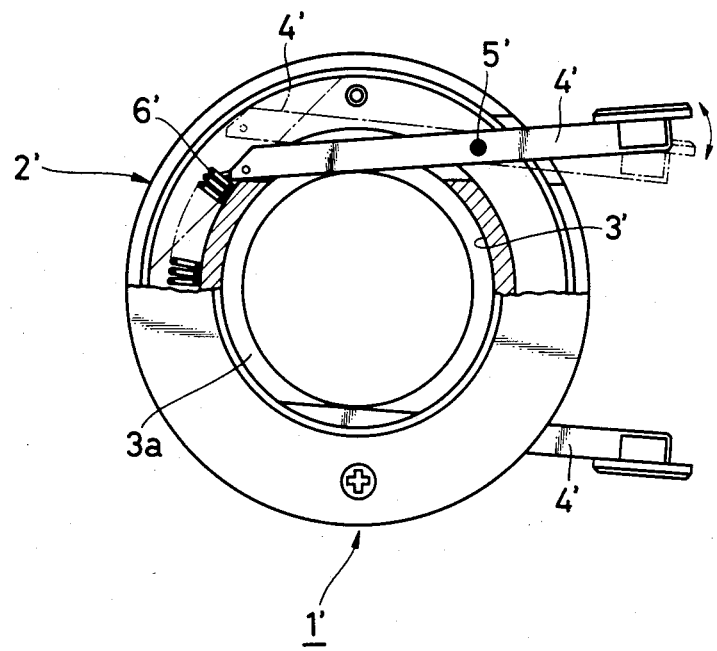
FIG. 13 is a partially cross-sectional, front elevational view showing a conventional connector device.
Figure 14:
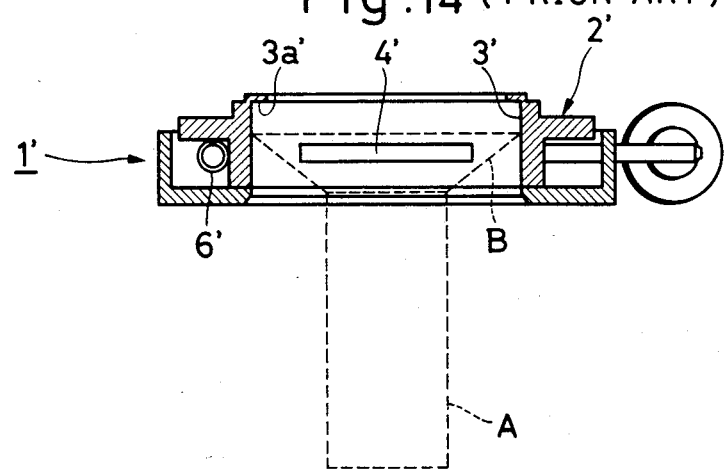
FIG. 14 is a cross-sectional view taken along a line perpendicular to an axis of an attaching ring shown in FIG. 13.

(FIGS. 13 and 14)

As is well known, an endoscope is utilized to observe a cavity of a human body. In order to photograph an observed image of the cavity, a photographing apparatus is adapted to be detachably connected to an eyepiece barrel of the endoscope by means of a connector device. A number of such connector devices have been proposed and utilized.

As shown in FIGS. 13 and 14, for example, a conventional connector device, generally designated by the reference numeral 1', comprises a tubular attaching ring 2' which is formed at a center thereof with a recess 3' having a diameter slightly greater than an outer diameter of an end flange B of an eyepiece barrel A. A pair of clamping links 4' and 4' are pivotally mounted, at their respective mid portions, on the attaching ring 2' by means of respective pins 5' such that the recess 3' is located between the pair of clamping links 4' and 4'. A resilient element or tension spring 6' abuts against an outer periphery of the attaching ring 2' and has opposite ends respectively anchored to respective tips of the pair of clamping links 4' and 4', to bias the clamping links 4' and 4' so as to cause the same to extend into the recess 3'. The connector device 1' is adapted to be secured to a photographing apparatus (not shown) such as a camera or the like by suitable fastening means. An annular end flange extends radially inwardly from an axial end of the attaching ring 2' which is to be located adjacent the camera, to provide an annular bottom surface 3a' of the recess 3'.

When the photographing apparatus having the connector device 1' secured thereto is attached to the eyepiece barrel A, respective outer ends of the pair of clamping links 4' and 4' are urged toward each other against the tension force of the spring 6'. This causes each clamping link 4' to be angularly moved around the corresponding pin 5' to a position indicated by the dot-and-dash line in FIG. 13, to fully open the recess 3' in the attaching ring 2'. With the recess 3' being fully open, the end flange B of the eyepiece barrel A is inserted into the recess 3' and, subsequently, the urging force is released from the clamping links 4' and 4'. The clamping links 4' and 4' are returned to their original positions under the action of the spring 6'. Each clamping link 4' extends into the recess 3', abuts against a tapered surface of the end flange B, and is urged thereagainst. In this manner, the end flange B is clamped between the clamping links 4' and 4' and the bottom surface 3a' by means of the resilient force of the tension spring 6', so that the photographing apparatus having secured thereto the connector device 1' is attached to the eyepiece barrel.

When the photographing apparatus is removed from the eyepiece barrel A, the pair of clamping links 4' and 4' are moved to the open position in the same manner as mentioned above.

With the construction of the above-described conventional connector device 1', when the photographing apparatus is to be attached to and removed from the eyepiece barrel A, it is required that an operator operates by his one hand to open the pair of clamping links 4' and 4' and by his other hand to hold the photographing apparatus, so that the operator cannot hold the endoscope. Thus, the attaching and removal operability is extremely low.

In addition, the tension spring 6' has a strong or high spring force, in order to fix the end flange B of the eyepiece barrel A within the attaching ring 2'. Accordingly, a strong force is required for the operator to open the pair of clamping links 4' and 4' against the tension force of the spring 6'. Thus, the operability is low, and it has been difficult to easily perform the attaching and removing operations.

OBJECT AND SUMMARY OF THE INVENTION

An object of the present invention is to provide a connector device which can substantially overcome the above-described disadvantages.

According to the present invention, there is provided a connector device for detachably connecting a photographing apparatus to an eyepiece barrel of an endoscope, the eyepiece barrel having an end flange, the connector device comprising: an attaching ring adapted to be secured to the photographing apparatus, the attaching ring having therein a space for receiving the end flange of the eyepiece barrel; a positioning surface located adjacent axial one end of the attaching ring for positioning an end face of the end flange of the eye piece barrel; a pair of clamping links disposed adjacent the other axial end of the attaching ring with the space in the attaching ring being located between the pair of clamping links, the pair of clamping links having their respective one ends pivotally mounted on the attaching ring so as to be pivotally movable in a plane substantially perpendicular to an axis of the attaching ring between an open position where the pair of clamping links are out of the space and a closed position where the pair of clamping links extend into the space in the attaching ring; resilient means for biasing the pair of clamping links toward each other; a pair of support links having their respective one ends pivotally connected to each other at a first connecting point and the respective other ends pivotally connected to the respective other ends of the pair of clamping links at second and third connecting points, respectively; stopper means associated with an assembly of the clamping and support links for maintaining the first connecting point in an inward position where the first connecting point is located between the axis of the attaching ring and a line passing through the second and third connecting points and for maintaining the pair of clamping links in the open position against the biasing force of the resilient means; and a force converting mechanism engageable with the end flange of the eyepiece barrel when the same is received in the space in the attaching ring and is moved toward the positioning surface, for converting a moving force of the end flange into a force substantially parallel to the plane to laterally urge the first connecting point to an outward position where the line is located between the axis of the attaching ring and the first connecting point, to release the assembly from the stopper means to allow the pair of clamping links to be moved to the closed position by the biasing force of the resilient means.

DETAILED DESCRIPTION OF THE PREFERRED EMBODIMENT

(FIGS. 1-12)

A connector device in accordance with an embodiment of the present invention, generally designated by the reference numeral 1 in the drawings, is adapted to be secured to a photographing apparatus (not shown) such as a camera or the like, for detachably connecting the photographing apparatus to an eyepiece barrel A (FIGS. 6, 7 and 9) of an endoscope (not shown).

The connector device 1 comprises an attaching ring 2 which has formed at a center thereof a space or recess 3 having a diameter slightly greater than an outer diameter of an end flange B of the eyepiece barrel A. An annular projection 2b extends radially inwardly from an axial end of the attaching ring 2 which is to be located adjacent the photographing apparatus, to provide an annular bottom surface 3a serving as a positioning surface against which an end face of the end flange B is to abut. An annular flange 2a extends radially outwardly from the opposite axial end of the attaching ring 2. A pair of clamping links 4 and 4 are disposed on the flange 2a so as to face to each other with the recess 3 being located between the pair of clamping links 4 and 4.

Figure 2:
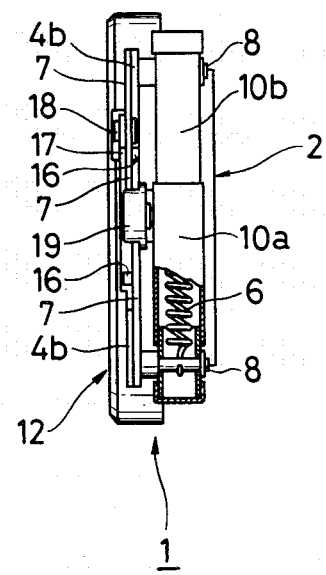
FIG. 2 is a partially cross-sectional, side elevational view of the connector device shown in FIG. 1.
Figure 3:
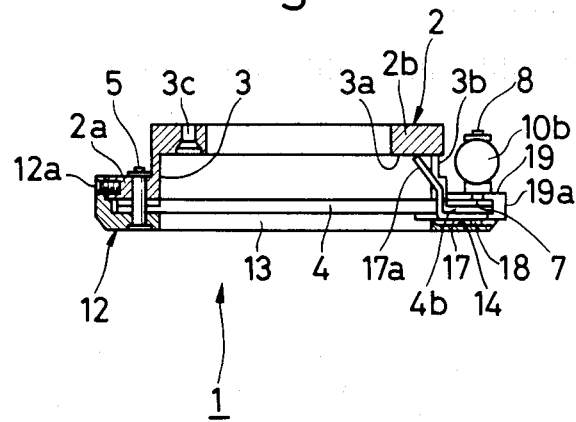
FIG. 3 is a cross-sectional view taken generally along a line perpendicular to an axis of an attaching ring shown in FIG. 1.
Figure 8:
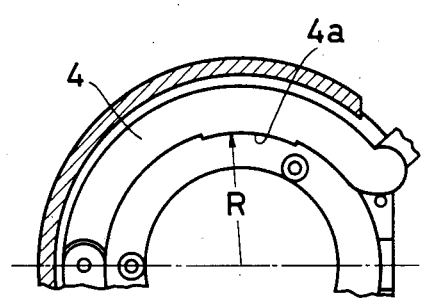
FIG. 8 is a fragmental cross-sectional front elevational view illustrating a radius of curvature of the clamping links.
Figure 9:
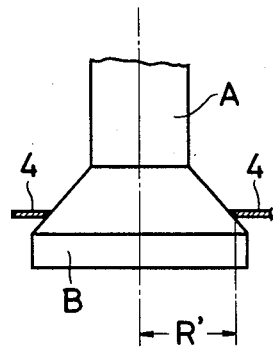
FIG. 9 is a fragmental cross-sectional view showing the clamping links abutting against a tapered surface of the end flange of the eyepice barrel.

Each of the pair of clamping links 4 and 4 has a semicircular configuration and has a radius of curvature substantially identical with a radius of the recess 3. The clamping links 4 and 4 have their respective one ends pivotally connected to the flange 2a by means of a common pivot pin 5 so as to be pivotable toward and away from each other in a plane substantially perpendicular to an axis of the attaching ring 2 between an open position shown in FIGS. 1–3 where the clamping links 4 and 4 are out of the recess 3 and a closed position shown in FIGS. 4 and 5 where the clamping links 4 and 4 extend into the recess 3. Each clamping link 4 has an arcuate projection 4a formed on or near its mid portion slightly extending inwardly from an inner edge of the clamping link. The projection 4a is located at a position angularly offset approximately 90 degrees from the pivot axis provided by the pin 5. As shown in FIGS. 8 and 9, the inner surface of the arcuate projection 4a is formed so as to have a radius of curvature R equal to or slightly less than a radius R' from a center line of the eyepiece barrel A or an axis of the attaching ring 2 to an abutting point when the end flange B of the eyepiece barrel A is fully received in the recess 3 in the attaching ring 2 and the arcuate projections 4a and 4a on the respective clamping links 4 and 4 abut against a tapered surface or the end flange B on the eyepiece barrel A, as described later with reference to FIGS. 4 and 5.

The pair of clamping links 4 and 4 has the respective other ends 4b and 4b which are bent and extend outwardly beyond the flange 2a of the attaching ring 2 so as to diverge away from the axis of the attaching ring 2. A step 15 is formed at the bent portion of each clamping link 4 and constitutes a first stopper mechanism having a function described later. A pair of support links 7 and 7 have their respective one ends pivotally connected to each other by a pivot pin 9 at a first connecting point and respective other ends pivotally connected to the respective other ends 4b and 4b of the pair of clamping links 4 and 4 by pivot pins 8 and 8 at second and third connecting points, respectively. Thus, the links 4 and 4 and 7 and 7 form a four-node limited linkage.

A resilient element or tension coil spring 6 has opposite ends thereof respectively anchored to the pins 8 and 8 which connect the respective other ends of the support links 7 and 7 and the respective other ends of the clamping links 4 and 4, respectively. The tension spring 6 is received in a pair of cylindrical housings 10a and 10b which are different in diameter from each other and are inserted into each other in a telescopic manner. The housings 10a and 10b have their axial ends which are remote from each other and which are supported by the pins 8 and 8, respectively.

A cover 12 is fastened to the flange 2a of the attaching ring 2 by means of screws 12a. The pair of clamping links 4 and 4 are housed between the cover 12 and the flange 2a. The cover 12 has therein an opening 13 of the same diameter as that of the recess 3 in the attaching ring 2. In addition, a lateral opening 14 is also formed in a side of the cover 12 which is adjacent the respective other ends 4b and 4b of the pair of clamping links 4 and 4. The other end 4b of each clamping link 4 extends outwardly from the lateral opening 14.

A pair of stoppers 16 and 16 extend axially from a portion of the flange 2a of the attaching ring 2, which portion is located between the respective other ends 4b and 4b of the pair of clamping links 4 and 4. The pair of stoppers 16 and 16 serve as a second stopper mechanism having a function described later.

A lateral opening 3b is formed in a side of the attaching ring 2 which is adjacent the respective other ends 4b and 4b of the pair of clamping links 4 and 4. An L-shaped link 17 which constitutes a force converting mechanism has one leg pivotally connected to one of the pair of support links 7 and 7 at a mid section thereof. The other leg of the L-shaped link 17 has a tip portion which is bent to provide a tapered surface 17a. The tapered surface 17a passes through the opening 3b and extends into the recess 3. A cut-out 17b is formed in the L-shaped link 17 so as to be capable of receiving the pin 9 which connects the pair of support links 7 and 7 to each other. An actuating member 19 is mounted to the pin 9 and has an urging portion 19a located outwardly of the respective one ends of the pair of support links 7 and 7.

Additionally, a plurality of bores 3c are formed through the bottom surface 3a of the recess 3 in the attaching ring 2 to allow screws to be respectively received in the bores 3c to securely fasten the attaching ring 2 to the photographing apparatus such as a camera or the like (not shown).

Figure 1:
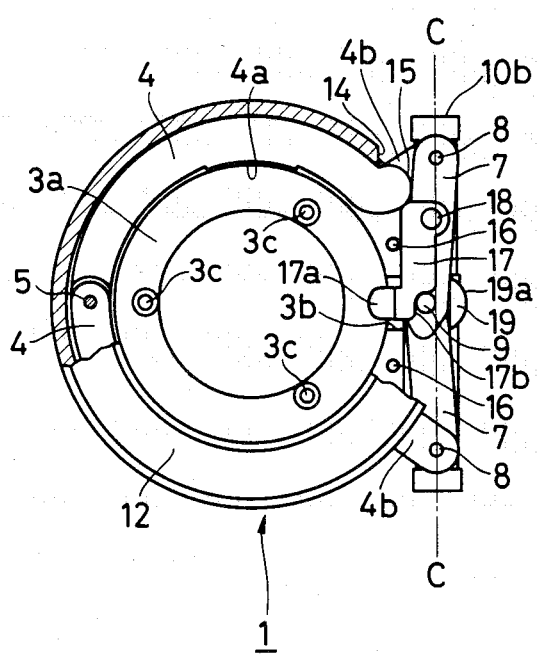
FIG. 1 is a partially cross-sectional, front elevational view of a connector device in accordance with an embodiment of the present invention, with a pair of clamping links being in an open position.

With the above-described construction and arrangement, the connector device 1 is initially in an open position shown in FIG. 1 where the single pin 9 (first connecting point) connecting the pair of support links 7 and 7 to each other is located inwardly of a line C—C shown by the dot-and-dash line in FIG. 1, passing through the two pins 8 and 8 (second and third connecting points) connecting the support links 7 and 7 and the clamping links 4 and 4, respectively, with the pin 9 being located between the line C—C and the axis of the attaching ring 2, and the clamping links 4 and 4 do not extend into the recess 3, i.e., are out of the recess 3, so that the recess 3 is fully open. The open position is maintained by the respective abutment of the support links 7 and 7 against the steps 15 and 15 on the respective clamping links 4 and 4.

Figure 6:
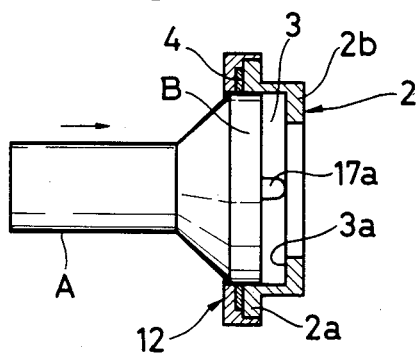
FIG. 6 is a fragmental cross-sectional view illustrating an end flange of an eyepiece barrel being received in a recess in the attaching ring.
Figure 7:
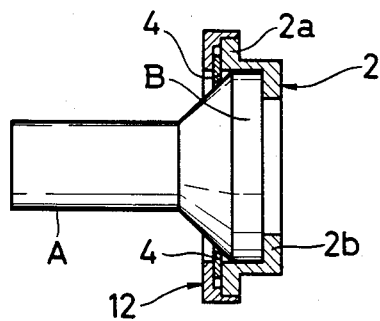
FIG. 7 is a view similar to FIG. 6, but showing the end flange fully received in the recess with an end face of the end flange abutting against a bottom surface of the recess.

When the photographing apparatus is desired to be attached to the eyepiece barrel A of the endoscope, an operator holds the photographing apparatus by his one hand and the endoscope by his other hand, and inserts the end flange B of the eyepiece barrel A into the recess 3 of the connector device 1, as shown in FIG. 6. As shown in FIG. 7, the end face of the end flange B abuts against the tapered suffice 17a of the L-shaped link 17, so that the tapered surface 17a converts the moving force of the end flange B into a force causing the end flange B to urge the tapered surface 17a outwardly. This causes the L-shaped link 17 to be angularly moved around the pin 18 and causes the cut-out 17b in the L-shaped link 17 to move the pin 9 outwardly, to thereby release the pair of support links 7 and 7 from the respective steps 15 and 15.

Figure 4:
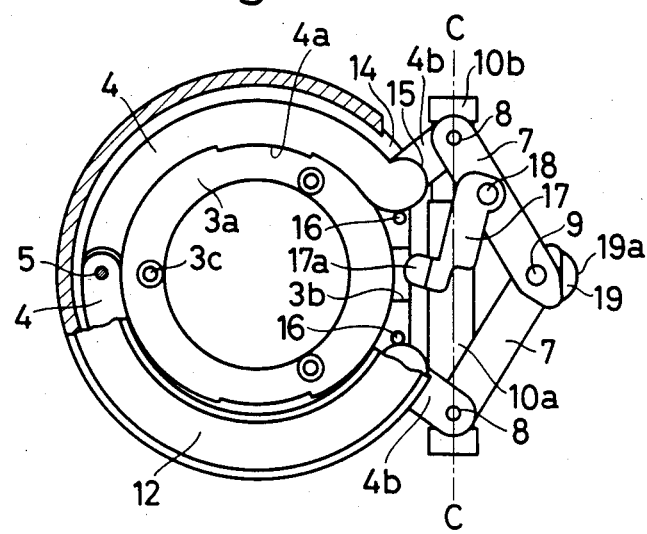
FIG. 4 is a view similar to FIG. 1, but showing the pair of clamping links in a closed position.
Figure 5:
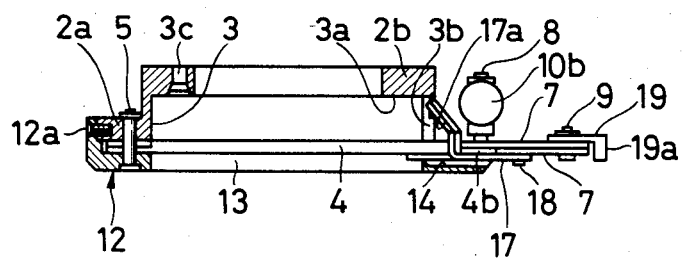
FIG. 5 is a cross-sectional view taken generally along a line perpendicular to the axis of the attaching ring shown in FIG. 4.

As the pin 9 is moved beyond a dead center, i.e., is moved to a position outwardly of the line C—C, shown by the dot-and-dash line in FIG. 4, passing through the two pins 8 and 8 connecting the support links 7 and 7 and the clamping links 4 and 4 to each other, the pair of support links 7 and 7 are angularly moved automatically around the respective pins 8 and 8 under the tension force of the spring 6, and the pair of clamping links 4 and 4 are angularly moved around the pin 5 to the open position shown in FIGS. 4 and 5 where the single pin 9 connecting the pair of support links 7 and 7 to each other is located outwardly of the line C—C passing through the two pins 8 and 8 with the line C—C being located between the axis of the attaching ring 2 and the pin 9, and the clamping links 4 and 4 extend into the recess 3.

Before the respective other ends 4b and 4b of the clamping links 4 and 4 abut respectively against the pair of stoppers 16 and 16, the respective arcuate projections 4a and 4a abut against the tapered surface of the end flange B and clamp the same by the tension force of the spring 6. Accordingly, the end face of the end flange B on the eyepiece barrel A is urged against the bottom surface 3a of the recess, so that the end flange B of the eyepiece barrel A is positively and securely held between the bottom surface 3a and the arcuate projections 4a and 4a without coming out of the recess 3. Thus, the photographing apparatus can be easily attached to the eyepiece barrel A by an operation only of the insertion of the end flange B of the eyepiece barrel A into the recess 3 in the attaching ring 2.

In addition, because of the arcuate projection 4a, 4a of the clamping links 4 and 4 can clamp the end flange B of the eyepiece barrel A at the respective mid portions of the clamping links, or portions remote from the pin 5, i.e., at a high angular moment, so that the end flange B can be securely fixed in position. Moreover, since the radius of curvature R of each arcuate projection 4a is set as stated previously, the arcuate projection 4a abuts against the tapered surface of the end flange B along the entire length of the projection 4a or at two points thereon, so that the fixing of the end flange B can be made further reliable.

Additionally, even if, when the connector device 1 is in the open position where the clamping links 4 and 4 are moved outwardly to fully open the recess 3, the tapered surface 17a of the L-shaped link 17 is inadvertently urged by a finger of an operator or the like, the connector device 1 would be operated in the manner as described above. In this case, however, the clamping links 4 and 4 would abut against the stoppers 16 and 16, respectively, and would be maintained in their respective positions where the links 4 and 4 extend into the recess 3 by a predetermined amount.

Moreover, when the photographing apparatus is desired to be removed from the eyepiece barrel A, the operator holds the photographing apparatus by his one hand and the endoscope by his other hand, and lightly pushes the urging portion 19a of the actuating member 19 inwardly by a finger of his hand which holds the photographing apparatus. This allows the single pin 9 connecting the pair of support links 7 and 7 to each other, to be moved from the outward position to the inward position with respect to the line C—C passing through the two pins 8 and 8, so that the connector device 1 is again brought into the open position. That is, the pair of clamping links 4 and 4 are angularly moved away from each other and are housed between the flange 2a of the attaching ring 2 and the cover 12. Thus, the recess 3 is fully open and the fixing of the end flange B of the eyepiece barrel A is released. In this manner, the mere pushing of the actuating member 19 allows the photographing apparatus to be removed from the eyepiece barrel A.

In addition, since the pair of support links 7 and 7 form a force-multiplier (toggle joint mechanism) of a kind, it is possible to move the pin 9 by a small force against the high resilient force of the tension spring 6, to allow the photographing apparatus to be attached to and removed from the endoscope.

Figure 10:
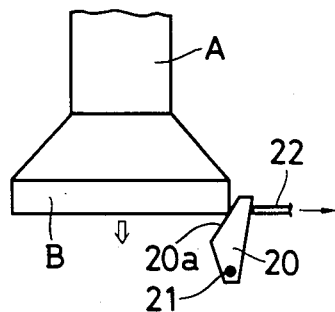
FIG. 10 is a fragmental view showing a modification of a force converting mechanism shown in FIG. 1.
Figure 11:
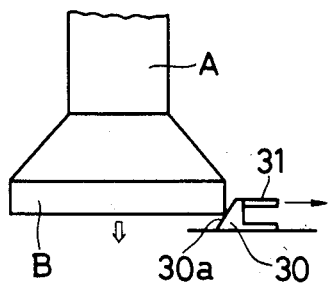
FIG. 11 is a fragmental view showing a further modification of the force converting mechanism.
Figure 12:
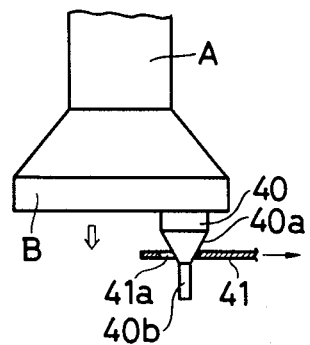
FIG. 12 is a fragmental cross-sectional view showing a still further modification of the force converting mechanism.

FIGS. 10 through 12 illustrate various modifications of the force converting mechanism.

In the modification shown in FIG. 10, a link 20 is supported in position on an attaching ring, corresponding to the attaching ring 2 shown in FIG. 1, by means of a pin 21 so as to be pivotable in a plane including the axis of the attaching ring. An operating member 22 has one end thereof engageable with the link 20 and the other end engageable with a pin, corresponding to the pin 9 shown in FIG. 1. As the end flange B of the eyepiece barrel A is inserted into the attaching ring, the end flange B abuts against a tapered surface 20a of the link 20 to convert the moving force of the end flange into a force directed perpendicularly of the axis of the attaching ring to move the operating member 22 outwardly, to thereby cause the same to urge the pin outwardly.

In the modification shown in FIG. 11, a slide link 30 is mounted on an attaching ring, similar to the attaching ring 2 shown in FIG. 1, so as to be slidable toward and away from the axis of the attaching ring. An operating member 31 has one end thereof engageable with the slide link 30 and the other end engageable with a pin 20 similar to the pin 9 shown in FIG. 1. As the end flange B of the eyepiece barrel A is inserted into the attaching ring, the end flange B abuts against a tapered surface 30a of the link 30 to convert the moving force of the end flange B into a force directed laterally to move the operating member 30 outwardly, to thereby cause the same to urge the pin outwardly.

In the modification shown in FIG. 12, a member 40 of a generally frustoconical shape is mounted on an attaching ring like the attaching ring 2 shown in FIG. 1 so as to be movable along the axis of the attacing ring. The frustoconical member 40 is inserted into a bore 41a in an oeprating member 41 from a reduced-diameter portion 40b of the frustoconical member 40. The operating member 41 has an end thereof remote from the bore 41a, which is engageable with a pin like the pin 9 shown in FIG. 1. As the end flange B of the eyepiece barrel A is inserted into the attaching ring, the end surface of the end flange B urges the frustoconical member 40 to cause a tapered or frustoconical surface 40a of the member 40 to abut aginst the bore 41a in the operating member 41, to convert the moving force of the end flange B into a lateral force to move the operating member 41 outwardly, to thereby cause the same to urge the pin outwardly.

The present invention should not be limited to the embodiment described above with reference to the accompanying drawings, but various modifications and changes can be made to the present invention. For example, each of the pair of clamping links may have one end thereof pivotally connected to the attaching ring through a separate pin. In addition, the positioning surface against which the end flange of the eyepiece barrel abuts may be provided on a body of the photographing apparatus. Additionally, the photographing apparatus may include a television camera other than a photographing camera.

As described above, in accordance with the present invention, it is possible to easily attach or mount the photographing apparatus to the eyepiece barrel of the endoscope by the mere insertion of the end flange of the eyepiece barrel into the attaching ring, and an operation of the connector device per se is unnecessary for the attachment of the photographing apparatus.

In addition, when the photographing apparatus is desired to be removed from the eyepiece barrel, a great force is not required for an operator's operation of the removal of the photographing apparatus from the eyepiece barrel. Thus, it is possible for the operator to easily perform the removal operation by only his single hand holding the photographing apparatus.

What is claimed is:

1. A connector device for detachably connecting a photographing apparatus to an eyepiece barrel of an endoscope, said eyepiece barrel having an end flange, said connector device comprising:

an attaching ring adapted to be secured to said photographing apparatus, said attaching ring having therein a space for receiving the end flange of said eyepiece barrel;

a positioning surface located adjacent one axial end of said attaching ring for positioning an end face of the end flange of said eyepiece barrel;

a pair of clamping links disposed adjacent the other axial end of said attaching ring with said space in said attaching ring being located between said pair of clamping links, said pair of clamping links having their respective one ends pivotally mounted on said attaching ring so as to be pivotally movable in a plane substantially perpendicular to an axis of said attaching ring between an open position where said pair of clamping links are out of said space and a closed position where said pair of clamping links extend into said space in said attaching ring;

resilient means for biasing said pair of clamping links toward each other;

a pair of support links having their respective one ends pivotally connected to each other at a first connecting point and the respective other ends pivotally connected to the respective other ends of said pair of clamping links at second and third connecting points, respectively;

stopper means associated with an assembly of said clamping and support links for maintaining said first connecting point in an inward position where said first connecting point is located between the axis of said attaching ring and a line passing through said second and third connecting points and for maintaining said pair of clamping links in said open position against the biasing force of said resilient means; and a force converting mechanism engageable with the end flange of said eyepiece barrel when the same is received in said space in said attaching ring and is moved toward said positioning surface, for converting a moving force of said end flange into a force substantially parallel to said plane to laterally urge said first connecting point to an outward position where said line is located between the axis of said attaching ring and said first connecting point, to release said assembly from said stopper means to allow said pair of clamping links to be moved to said closed position by the biasing force of said resilient means.

2. A connector device as defined in claim 1, wherein the respective one ends of said pair of clamping links are pivotally connected to said attaching ring through a common pivot pin.

3. A connector device as defined in claim 2, wherein said pair of clamping links have a substantially semi-circular configuration and cooperate with each other to partially surround said space in said attaching ring, each of said clamping links having thereon and arcuate projection at a position angularly offset from said common pivot pin approximately 90 degrees, said arcuate projection extending toward the axis of said attaching ring.

4. A connector device as defined in claim 3, wherein said arcuate projection has a radius of curvature substantially identical with a radius of that portion of said end flange on said eyepiece barrel which is engaged by said arcuate projection on each clamping link, when the end face of said end flange abuts against said positioning surface and said pair of clamping links are moved to said closed position.

5. A connector device as defined in claim 4, wherein the respective other ends of said pair of clamping links are bent so as to diverge away from the axis of the attaching ring, said stopper means comprising a step at the bent portion of each of said clamping links.

6. A connector device as defined in claim 1, further comprising second stopper means on said attaching ring, said pair of clamping links being engageable with said second stopper means when said end flange of said eyepiece barrel is not received in said space in said attaching ring and said first connecting point is inadvertently urged to said outward position.

7. A connector devide as defined in claim 1, further comprising an actuating member mounted to said first connecting point, said actuating member being manually operable to move said first connecting point from said outward position to said inward position.

8. A connector device as defined in claim 1, wherein said stopper means is provided on said pair of clamping links.

9. A connector device as defined in claim 1, wherein said space is comprised of a recess formed in said attaching ring, and said positioning means is comprised of a bottom surface of said recess.

10. A connector device as defined in claim 1, wherein said force converting meachanism comprises an L-shaped link having one leg pivotally connected to one of said pair of support links so as to be pivotable in a plane substantially perpendicular to the axis of said attaching ring, the other leg of said L-shaped link having a tapered surface, said L-shaped link being engageable with said first connecting point when the same is in said, inward position, said tapered surface being engaged by said end flange of said eyepiece barrel when the same is received in said space in said attaching ring, to cause said L-shaped link to urge said first connecting point toward said outward position.

11. A connector devide as defined in claim 1, wherein said force converting mechanism comprises a tapered link connected to said attaching ring so as to be pivotable in a plane including the axis of said attaching ring, and an operating member having one end thereof engageable with said tapered link and the other end engageable with said first connecting point, said tapered link being engaged by said end flange of said eyepiece barrel when the same is received in said space in said attaching ring, to cause said operating member to urge said first connecting point toward said outward position.

12. A connector device as defined in claim 1, wherein said force converting mechanism comprises a tapered slide link slidable toward and away from the axis of said attaching ring and an operating member having one end thereof engageable with said tapered slide link and the other end engageable with said first connecting point, said tapered slide link being engaged by said end flange of said eyepiece barrel when the same is recieved in said space in said attaching ring, to cause said operating member to urge said first connecting point toward said outward position.

13. A connector device as defined in claim 1, wherein said force converting mechanism comprises a frustoconical member movable substantially along the axis of said attaching ring and an operating member having one end thereof engageable with said frustoconical member and the other end engageable with said first connecting point, said frustoconical member being engaged by said end flange of said eyepiece barrel when the same is received in said space in said attaching ring, to cause said operating member to urge said first connecting point toward said outward position.

* * * * *